United States Patent
Aquino et al.

(10) Patent No.: US 7,601,877 B2
(45) Date of Patent: Oct. 13, 2009

(54) PROCESS FOR THE PREPARATION OF UBIHYDROQUINONES AND UBIQUINONES

(75) Inventors: Fabrice Aquino, Reiningue (FR); Werner Bonrath, Freiburg (DE); Patrick Bohrer, Hegenheim (FR); Max Hugentobler, Arlesheim (CH); Thomas Netscher, Bad Krozingen (DE); Alexander Radspieler, Grenzach-Wyhlen (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 11/997,326

(22) PCT Filed: Aug. 2, 2006

(86) PCT No.: PCT/EP2006/007645

§ 371 (c)(1),
(2), (4) Date: Feb. 19, 2008

(87) PCT Pub. No.: WO2007/017168

PCT Pub. Date: Feb. 15, 2007

(65) Prior Publication Data

US 2008/0275275 A1    Nov. 6, 2008

(30) Foreign Application Priority Data

Aug. 10, 2005  (EP) .................................. 05017374

(51) Int. Cl.
   *C07C 45/61*    (2006.01)
(52) U.S. Cl. ...................................................... 568/362
(58) Field of Classification Search .................. 568/362
   See application file for complete search history.

(56) References Cited

U.S. PATENT DOCUMENTS 4,039,573 A    8/1977    Kijima et al.

OTHER PUBLICATIONS

International Search Report for PCT/EP2006/007645 mailed Feb. 1, 2007.
Written Opinion for PCT/EP2006/007645 mailed Feb. 1, 2007.

*Primary Examiner*—Sikarl A Witherspoon
(74) *Attorney, Agent, or Firm*—Nixon & Vanderhye P.C.

(57) ABSTRACT

A process for the preparation of ubihydroquinones and ubiquinones by condensation of a prenol or isoprenol with a hydroquinone or derivative thereof in the presence of 0.005-1.0 mol % of a catalyst which is a Broensted-acid, a Lewis-acid from the group consisting of a derivative of Bi or In or an element of group 3 of the periodic table of the elements, a heteropolyacid, an NH— or a CH-acidic compound, and optionally oxidizing the ubihydroquinone obtained.

14 Claims, No Drawings

PROCESS FOR THE PREPARATION OF UBIHYDROQUINONES AND UBIQUINONES

This application is the U.S. national phase of International Application No. PCT/EP2006/007645 filed 2 Aug. 2006 which designated the U.S. and claims priority to European Patent Application No. 05017374.9 filed 10 Aug. 2005, the entire contents of each of which are hereby incorporated by reference.

Ubiquinones are prenylated quinones which are present in nearly all organisms, in plants and animals including humans, and known since 1956. They are part of the inner membrane of mitochondria and bacterial membranes serving as transmitters of electrons and protons in the respiratory chain where they are reversibly transformed into corresponding hydroquinones (ubiquinols) via semiquinones.

Ubiquinones, also known as coenzymes Q (CoQ), are designated according to the number of the isoprenyl units of their side chain Q-1, Q-2, Q-3, etc. (or CoQ1, CoQ2, CoQ3, etc.) or according to the number of the carbon atoms of their side chain U.-5, U.-10, U.-15, etc. In *Escherichia coli* Q-1 to Q-8 have been found, in fish Q-9 and in rat Q-11 and Q-12. In most mammals including humans Q-10 is predominant and, therefore, has attracted most interest.

Ubiquinones, especially the higher ones, CoQ8 to CoQ12, and particularly CoQ10, are widely used, e.g., in the treatment and prevention of various diseases such as heart and neurological diseases, in cosmetics and as food or dietary supplements. Ubiquinoles as part of the ubiquinone/ubiquinole redox-system are natural antioxidants.

O. Isler and co-workers were the first to synthesize U.-45 (Q-9) and U.-50 (Q-10) from 5-methyl-2,3-dimethoxy-hydroquinone and solanesol (contained in tobacco leaf) or the corresponding isoprenoid compound obtained by extending solanesol by one isoprenyl unit, respectively, in diethyl ether in the presence of $ZnCl_2$ as catalyst and oxidizing the resulting condensation product with $Ag_2O$ (Helv. Chim. Acta 42, 2616-2621 [1959]).

H. Fukawa et al. in U.S. Pat. No. 3,549,668 describe the preparation of coenzymes $Q_9$-$Q_{12}$. Solanesol or isoprenyl alcohols corresponding to $Q_9$, $Q_{11}$ and $Q_{12}$, extracted from Silkworm feces or 24.05.2006/Mez/sk mulberry leaves, are condensed in the presence of $ZnCl_2$, $AlCl_3$ and $BF_3$ ether complex with 5-methyl-2,3-dimethoxy-hydroquinone or its 4-acyl derivative and the ubihydroquinones obtained were oxidized according to the methods described by Isler et al.

S. Kijima et al. in U.S. Pat. No. 4,062,879 describe the preparation of coenzyme Q compounds by reaction of 2-methyl-4,5,6-trimethoxyphenol with boric acid or a reactive derivative thereof to form the corresponding borate which is then reacted with a prenol or isoprenol, hydrolysed and oxidized.

H. Eto et al. (Chemistry Letters 1988, 1597-1600) increased the yield to 51% (after purification 46%) and stereoselectivity (E/Z at the 2,3-double bond of the side chain=92:8, after purification >99:1) of the condensation reaction in the presence of $BF_3$ ether complex by using a hexane/nitromethane (1:2, v/v) mixture as solvent and a ten fold amount of isodecaprenol.

E. Morita et al. (DOS 28 09 496) describe a method for the preparation of 2-methyl-3-prenyl-4,5,6-trimethoxy-phenols (wherein the prenyl chain consists of 1-10 isoprenyl units) by reacting 2,3,4-trimethoxy-6-methyl-phenol with a poly-prenol of formula R—C($CH_3$)=CH—$CH_2$—OH or an isomer thereof of formula R—C($CH_3$)(OH)—CH=$CH_2$ in the presence of a catalyst containing a Lewis acid (such as $BF_3$ and ether complexes thereof, $ZnCl_2$, $AlCl_3$ and $SnCl_4$) and a $SiO_2$-$Al_2O_3$ compound. The prenylphenol obtained can easily be oxidized to give the corresponding 1,4-quinone using a mild oxidizing agent such as $Ag_2O$, $PbO_2$, $FeCl_3$ or aqueous $H_2O_2$.

The syntheses so far developed still use high amounts of catalysts in the condensation reaction, viz. up to 20 mol % (in the case of $BF_3$ ether complex; and even higher, e.g., with $ZnCl_2$ approximately 300 mol %). Other catalysts should be identified which in lower amounts give high yields with a high E/Z-ratio at the 2,3-double bond of the side chain thus making the technical process for the preparation of ubihydroquinones and ubiquinones more effective.

In accordance with the present invention it has now been found that this is achieved by the use of other catalysts, so far not used in this condensation reaction.

The present invention, therefore, relates to a process for the preparation of ubihydroquinones and ubiquinones of the formula

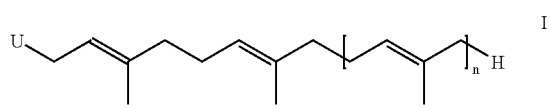

wherein U is the residue of a hydroquinone or quinone of formula

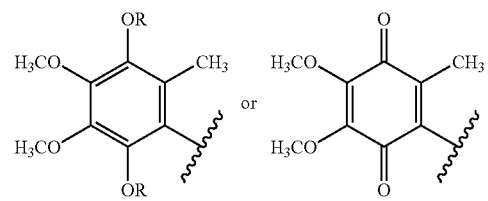

wherein R independently from each other are hydrogen or a lower alkyl group or both are tri-(lower alkyl)-silyl, lower alkanoic acyl groups or groups of the general formula —[($CH_2$)$_q$O]$_r$—($CH_2$)$_p$—O—($CH_2$)$_m$—H, m is 1 or 2; n is an integer of 6 to 10;

p is 1 or 2; q is 1 or 2 and r is 0 or 1, which process is characterized by reacting an isoprenol of formula

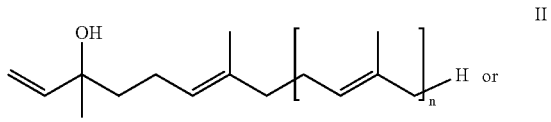

a prenol of formula

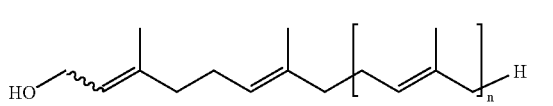

or a corresponding X-derivative, wherein OH is replaced by X and X is a leaving group, with a hydroquinone (R=H) or a hydroquinone derivative of formula

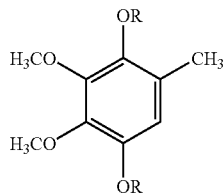

IV in an organic solvent in the presence of 0.005-1.0 mol %, relative to the isoprenol/prenol, of a catalyst which is a Broensted-acid, especially a sulfur(VI) containing acid, a Lewis-acid from the group consisting of a salt of Bi or In or an element of group 3 of the periodic table of the elements, a heteropoly acid, an NH- or a CH-acidic compound, and optionally oxidizing the ubihydroquinone obtained by the condensation.

The invention also relates to the use of these catalysts in the indicated amounts in the condensation reaction of an isoprenol of formula II or a prenol of formula III with a hydroquinone or derivative thereof of formula IV.

It is anticipated that these catalysts in the indicated amounts can also be used in analogous condensation reactions for the preparation of ubihydroquinols and ubihydroquinones of formula I wherein n is lower than 6 or higher than 10.

A preferred range of the amount of catalyst present in the condensation reaction is 0.05-0.7 mol % and an even more preferred range is 0.1-0.5 mol %.

The term lower alkyl relates to straight- or branched-chain alkyl groups with 1-6 carbon atoms, preferably methyl or ethyl. The preferred tri-(lower alkyl)-silyl group is trimethylsilyl. The term lower alkanoic acyl relates to lower alkyl carboxylic acids. The preferred lower alkanoic acyl group is acetyl. In etherified hydroquinone derivatives the group R can be methoxy- or ethoxy-methyl or -ethyl or a corresponding group extended by an oxymethyl or oxyethyl group, e.g., methoxy-methoxy-methyl, methoxy-methoxy-ethyl, methoxy-ethoxy-methyl, methoxy-ethoxy-ethyl, ethoxy-methoxy-methyl and ethoxy-methoxy-ethyl.

The hydroquinone starting material IV can, i.a., be 2,5-dihydroxy-3,4-dimethoxy-toluene, a 2 (or 5)-hydroxy-3,4-dimethoxy-5 (or 2)-lower alkoxy-toluene, e.g. 2-hydroxy-3,4,5-trimethoxytoluene or 2,3,4-trimethoxy-5-hydroxytoluene, a 2,5-di-(lower alkoxy)-3,4-dimethoxy-toluene, e.g., 2,3,4,5-tetramethoxytoluene, a 2,5-bis-(tri-(lower-alkyl)-silyloxy)-3,4-dimethoxy-toluene, e.g., 2,5-bis-(trimethylsilyloxy)-3,4-dimethoxy-toluene or a 2,5-di-(lower alkanoyloxy)-3,4-dimethoxy-toluene, e.g., 2,5-diacetyloxy-3,4-dimethoxy-toluene.

n encompasses the integers 6, 7, 8, 9 and 10 with 8 being preferred because it defines coenzyme Q10 as a compound of formula I.

It is evident to the person skilled in the art that derivatives of an isoprenol of formula II and a prenol of formula III can also be used in the condensation reaction, viz. compounds of formulae

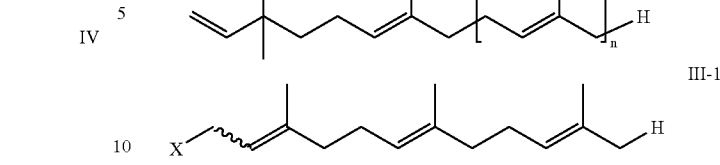

wherein X is a leaving group, e.g., acetate, chloride or bromide.

The condensation reaction is carried out in a solvent from the group consisting of monocylic aromatic hydrocarbons, e.g., toluene and xylenes; alkanes, which may be substituted, e.g., $C_{5-10}$-alkanes, such as a pentane, hexane, heptane, octane, nonane and decane, and nitro-$C_{1-4}$-alkanes, such as nitromethane, nitroethane and nitropropane; aliphatic ethers, e.g., diethylether and methyl tert. butyl ether; aliphatic ketones, e.g., acetone and diethyl ketone; lower-alkanoic acid lower-alkyl esters, e.g., methyl acetate and ethyl acetate; and di-(lower-alkyl)-carbonates or lower-alkylene carbonates, e.g., dimethyl and diethyl carbonate or ethylene, propylene and butylene carbonates, respectively. Preferably a two-phase system represented by a nitro-$C_{1-4}$-alkane and a $C_{6-8}$-alkane is used wherein the v/v-ratio is 1:1.5-5, preferably 1:1.8-2.5. A preferred reaction solvent system is nitromethane/heptane.

The mol-ratio of the reactants, IV:II or III, is in the range of 2.5-10:1, preferably 4-6:1.

The reaction is carried out in a manner known to the person skilled in the art, at a temperature of about 20-60° C., preferably at 30-55° C. in the case of isodecaprenol according to formula II or decaprenol according to formula III and 3,4-dimethoxy-2,5-dihydroxy-toluene in nitromethane/heptane during a time of from 30 minutes to 24 hours depending upon the amounts of reactants and catalyst as well as solvents used, under normal pressure. If desired, pressure can be increased up to several atmospheres.

The reaction can be carried out under an inert gas atmosphere, preferably under nitrogen or argon, batchwise or continuously.

The term Broensted acid refers to sulfuric acid, p-toluene-sulphonic acid, methanesulphonic acid, ethanesulphonic acid, fluorosulphonic acid and trifluoro-methanesulphonic acid.

The term Lewis acid refers to salts of In, Bi or an element of group 3 of the periodic table of elements. An element of group 3 of the periodic table means Sc, Y, La, and the lanthanoides (Ce, Pr, Nd, Pm, Sm, Eu, Gd, Tb, Dy, Ho, Er, Tm, Yb, Lu), among which Sc, La, Ce, Eu, Gd and Yb are preferred. Preferred are salts with hydrohalic acids, particularly hydrochloric acid and trifluoro-methanesulphonic acid, such as $InCl_3$, $BiCl_3$, In-triflate, Bi-triflate, La-triflate.

The term heteropolyacid refers to oxygen acids with P, As, Si, B or J as central atoms which are connected with W, Mo or V via oxygen bridges. Examples of such acids are tungsten and molybdenum phosphoric acid and tungsten and molybdenum arsenic acid. Preferred is $H_3PW_{12}O_{40}$.

The term NH-acidic compound refers to perfluoro lower-alkylsulfonyl imides as described in EP 1 180 517, especially of formula $HN(SO_2C_nF_{2n+1})_2$, wherein n is an integer of 1-10, preferably 1-4 and the perfluoroalkyl groups can be the same or are different from each other.

The term CH-acidic compound refers to perfluoro lower-alkylsulfonyl methanes as described in WO 2004/096790, especially of formula $HC(SO_2C_nF_{2n+1})_3$ wherein n is an integer of 1-4, and wherein the perfluoroalkyl groups can be the same or different from each other.

All catalysts are known compounds. They are commercially available or can be prepared in accordance with methods known in the art. The catalyst can be added to the reaction mixture in solid form, if desired on a well-known carrier, as described, e.g., in U.S. Pat. No. 4,062,879, or in form of a solution.

The starting materials of formulae IV and II or III as well as the corresponding acetates, chlorides and bromides are known compounds which are commercially available or can easily be prepared according to methods described in the literature or in analogy thereto.

The optional step of oxidation of the ubiquinol obtained by the condensation to the corresponding ubiquinone can be performed as described in the art under mild oxidation conditions. Preferred oxidation agents are air oxygen, $Ag_2O$, $FeCl_3$ or cerium(IV) ammonium nitrate.

The invention is described in more detail in the following examples.

HPLC was carried out with a HP-apparatus 1050 using a RP YMC-Pack ODS-A column 150 mm or 250 mm, diameter 4.6 mm; mobile phase methanol: hexane (80:20, v/v) for the determination of the yield (wt %) by using an external standard and, for the determination of the E/Z-ratio, 2 columns Spherisorb S3-W, 150 mm, diameter 4.6 mm, particle size 3 μm; 25° C.; mobile phase hexane: isopropanol (99.7:0.3, v/v) or hexane: 20% ethyl acetate in hexane containing 1% 2-methoxyethanol and 0.1% N-ethyl-diisopropylamine (9:1, v/v) for CoQ10 and CoQ9, respectively.

EXAMPLE 1

Preparation of CoQ10 by Condensation of IDP with DMDHT in Heptane/Nitromethane in the presence of Catalyst X and Subsequent Oxidation General Procedure Under argon atmosphere in a 200 ml four necked flask equipped with a KPG-stirrer, thermometer, gas inlet, and a reflux condenser, 5.14 mmol (3.59 g) of isodecaprenol (IDP) were dissolved in 75 ml of n-heptane and the solution was mixed with 25.69 mmol (4.73 g) of 3,4-dimethoxy-2,5-dihydroxytoluene (DMDHT) dissolved in 38 ml of nitromethane. 0.15-0.54 mmol of the catalyst, a Lewis-acid or heteropoly acid, were then added (in solid form or in solution). The two-phase mixture was heated up to 50° C. (internal temperature) under stirring (450 rpm). After 12 hours reaction time the mixture was cooled down to room temperature (21° C.). The heptane layer was separated and washed two times with 20 ml (total 40 ml) of nitromethane (to extract the excess of hydroquinone). The heptane phase was oxidised with 4.5 g of silver (I) oxide and 0.3 ml of glacial acetic acid for one hour at room temperature. The dark brown mixture was filtered (over Dicalite Speedex®, filter aid), washed with heptane, and evaporated under reduced pressure.

The isolated orange crude product (oil) was analyzed with HPLC and found to be CoQ10 in high yield and high E/Z ratio (2,3-double bond of the side chain).

In that way CoQ10 was prepared with the following amounts of reactants, catalysts and solvents:

IDP=4.8 mmol, DMDHT=24.1 mmol, nitromethane 25 ml, hexane 50 ml, $Sc(OTf)_3$=0.5 mmol, reaction temperature 53° C., yield CoQ10 47.4%, E/Z 94/6.

IDP=4.5 mmol, DMDHT=22.7, nitromethane 25 ml, heptane 50 ml, $NH(SO_2CF_3)_2$=0.5 mmol, reaction temperature 49° C., yield CoQ10 42.8%, E/Z 92/8.

IDP=4.9 mmol, DMDHT=24.3 mmol, nitromethane 26 ml, hexane 40 ml, $InCl_3$=0.54 mmol, reaction temperature 52.5° C., yield CoQ10 48.2%, E/Z 94.6.

IDP=2.4 mmol, DMDHT=12.1 mmol, nitromethane 13 ml, hexane 25 ml, $InCl_3$=0.41 mmol, reaction temperature 57° C., yield CoQ10 46.6%, E/Z 94/6.

IDP=4.8 mmol, DMDHT=12.1 mmol, nitromethane 25 ml, hexane 50 ml, $InCl_3$=0.40 mmol in water, reaction temperature 45° C., yield CoQ10 47.6%, E/Z 93/7.

IDP=2.4 mmol, DMDHT=24.1 mmol, nitromethane 13 ml, hexane 30 ml, $H_3PW_{12}O_{40}$=0.09 mmol, reaction temperature 52° C., yield CoQ10 47.2%, E/Z 93/7.

IDP=4.8 mmol, DMDHT=24.2 mmol, nitromethane 25 ml, hexane 50 ml, $H_3PW_{12}O_{40}$=0.15 mmol, reaction temperature 53° C., yield CoQ10 45.2% E/Z 93/7.

IDP=4.7 mmol, DMDHT=23.4 mmol, nitromethane 25 ml, heptane 50 ml, $La(OTf)_3$=0.51 mmol, reaction temperature 50° C., yield CoQ10 44.4%, E/Z 93/7.

IDP=4.7 mmol, DMDHT=23.4 mmol, nitromethane 25 ml, heptane 50 ml, $Eu(OTf)_3$=0.48 mmol, reaction temperature 50° C., yield CoQ10 43.4%, E/Z 93/7.

IDP=4.7 mmol, DMDHT=2.4 mmol, nitromethane 25 ml, heptane 50 ml, $Yb(OTf)_3$=0.56 mmol, reaction temperature 51° C., yield CoQ10 41.4%, E/Z 93/7.

IDP=4.7 mmol, DMDHT=23.4 mmol, nitromethne 25 ml, heptane 50 ml, $Ce(OTf)_3$=0.54 mmol, reaction temperature 50° C., yield COQ10 42.5%, E/Z 93/7.

IDP=4.7 mmol, DMDHT=23.4 mmol, nitromethane 25 ml, heptane 50 ml, $Gd(OTf)_3$=0.46 mmol, reaction temperature 50° C., yield COQ10 44%, E/Z 93/7.

IDP=4.7 mmol, DMDHT=23.4 mmol, nitromethane 25 ml, heptane 50 ml, $Bi(OTf)_3$=0.28 mmol, reaction temperature 50° C., yield CoQ10 35.6%, E/Z 93/7.

EXAMPLE 2

Preparation of CoQ10 by Condensation of IDP with TMHT in heptane/nitromethane in the presence of $Bi(OTf)_3$ and Subsequent Oxidation In a 200 ml four necked flask equipped with a KPG-stirrer, thermometer, gas inlet, and a reflux condenser, under argon atmosphere 2.4 mmol (1.68 g) of isodecaprenol (IDP) were dissolved in 25 ml of n-heptane and mixed with 11.8 mmol (2.34 g) of 3,4,5-trimethoxy-2-hydroxytoluene (TMHT) dissolved in 13 ml of nitromethane. The catalyst, $Bi(OTf)_3$ (0.09 mmol), was then added. The two-phase mixture was heated up to 46° C. (internal temperature) under stirring (450 rpm). After 12 hours reaction time the mixture was cooled down to room temperature (21° C.). The heptane layer was separated and washed two times with 10 ml (total 20 ml) of nitromethane. The heptane phase was evaporated (2.4 g crude product, yield 46.8%). Oxidation of a sample according to Example 3 (below) gave an E/Z ratio of CoQ10 of 96:4.

EXAMPLE 3

Oxidation of 2-hydroxy-3,4,5-trimethoxy-6-decaprenyl-toluene

In a 100 ml flask 1.09 g (0.91 mmol) of 73.3% 2-hydroxy-3,4,5-trimethoxy-6-decaprenyl-toluene were dissolved in 4.1 ml of dichloromethane and 4.1 ml acetonitrile at 0° C. To this solution 2.46 g $FeCl_3·6 H_2O$ (9.0 mmol, commercial from Riedel de Haen) in 8.2 ml of acetonitrile were added at 0-5° C.

After 30 minutes at 0-5° C., 60 ml deionised water were added and the orange emulsion after addition of 60 ml 5% aqueous NaHCO$_3$ solution was extracted with 250 ml of ether. The water layer was extracted with 60 ml of ether. The combined ether phases were dried over Na$_2$SO$_4$ and concentrated at 35° C. under reduced pressure (20 to 10 mbar). The crude product (orange oil, 1.09 g, 100%) was analysed by HPLC to be CoQ10; E/Z-ratio 95.8:4.2.

Using the same reaction conditions, however, in a solvent mixture of 8.2 ml of acetonitrile, 4.1 ml of dichloromethane, and 4.1 ml of deionised water, CoQ 10 was obtained in 100% yield; E/Z=95.8:4.2.

Using the same reaction conditions, however, in a solvent mixture of 0.4 ml of ethyl acetate and 1 ml of diisopropyl ether, COQ10 was obtained in 95% yield; E/Z=95.7:4.3.

Oxidation with 1.73 g (3.12 mmol) of cerium (IV) ammonium nitrate in 8.2 ml of acetonitrile, 4.1 ml of dichloromethane, and 4.1 ml of deionised water provided CoQ10 in 61% yield; E/Z=94.9:5.1.

EXAMPLE 4

Preparation of CoQ9 from DMDHT and Solanesol

In a 50 ml four necked flask equipped with a stirrer, thermometer, gas inlet, and a reflux condenser, under argon atmosphere 0.654 g (96.52%, 1 mmol) of solanesol (nonaprenol, C$_{45}$) were dissolved in 15 ml of n-hexane. The solution was mixed with 0.983 g (5.0 mmol) of 2,3-dimethoxy-1,4-dihydroxy-toluene (DMDHT) dissolved in 7.6 ml of nitromethane. The catalyst, Sc(OTf)$_3$ (2.5 mg, 0.005 mmol) was then added. The two-phase mixture was heated up to 50° C. (internal temperature) under stirring (400 rpm). After 16 hours reaction time the mixture was cooled down to room temperature (21° C.). The hexane layer was separated and washed two times with 4 ml (total 8 ml) of nitromethane. The hexane phase was evaporated and yielded 0.78 g of crude 2,3-dimethoxy-5-methyl-6-((2E,6E,10E,14E,18E,22E,26E, 30E)-3,7,11,15,19,23,27,31,35-nonamethyl-hexatriaconta-2,6,10,14,18,22,26,30,34-nonaenyl)-benzene-1,4-diol (H$_2$-CoQ9), which was purified by column chromatography on 30 g silica (elution with n-hexane/ethyl acetate=99/1, v/v), to give 440 mg of an orange oil consisting of 73.2% H$_2$-CoQ9 and 21% CoQ9 (formed from H$_2$-CoQ9 by partial air oxidation during isolation and HPLC analysis), corresponding to yields of 40.4% H$_2$-CoQ9 and 11.6% CoQ9, sum 52%.

This product mixture, dissolved in hexane was oxidized completely to the corresponding 1,4-quinone (CoQ9) as outlined in Example 1.

EXAMPLE 5

Preparation of CoQ9 from TMHT and Solanesol

In a 50 ml four necked flask equipped with a stirrer, thermometer, gas inlet, and a reflux condenser, under argon atmosphere 0.654 g (96.52 wt %, 1 mmol) of solanesol were dissolved in 15 ml of n-hexane and the solution was mixed with 1.2 g (5.0 mmol) of 3,4,5-trimethoxy-2-hydroxy-toluene (TMHT) dissolved in 7.6 ml of nitromethane.

The catalyst, Sc(OTf)$_3$ (2.5 mg, 0.005 mmol), was then added. The two-phase mixture was heated up to 50° C. (internal temperature) under stirring (400 rpm). After 16 hours reaction time the mixture was cooled down to room temperature (21° C.). The hexane layer was separated and washed two times with 4 ml (total 8 ml) of nitromethane. The hexane phase was evaporated and yielded 0.82 g of crude 2,3,4-trimethoxy-6-methyl-5-((2E,6E,10E,14E,18E,22E,26E, 30E)-3,7,11,15,19,23,27,31,35-nonamethyl-hexatriaconta-2,6,10,14,18,22,26,30,34-nonaenyl)-phenol as a colorless oil. Purification by column chromatography on 30 g silica (elution with n-hexane/ethyl acetate=99:1, v/v) yielded 440 mg of a colorless oil which crystallized upon standing; yield 51%, purity 94.6%.

Oxidation of the crude phenol to the corresponding 1,4-quinone (CoQ9) was performed by using FeCl$_3$ 6 H$_2$O similar to the published procedure of S. Kijima et al.

EXAMPLE 6

Preparation of CoQ9 from TMT and Solanesol

In a 50 ml four necked flask equipped with a stirrer, thermometer, gas inlet, and a reflux condenser, under argon atmosphere 0.654 g (96.52%, 1 mmol) of solanesol were dissolved in 15 ml of n-hexane and mixed with 1.07 g (5.0 mmol) of 2,3,4,5-tetramethoxy-toluene (TMT) suspended in 7.6 ml of nitromethane. The catalyst, Sc(OTf)$_3$ (2.5 mg, 0.005 mmol), was then added. The two-phase mixture was heated up to 50° C. (internal temperature) under stirring (400 rpm). After 16 hours reaction time the mixture was cooled down to room temperature (21° C.). The hexane layer was separated and washed two times with 4 ml (total 8 ml) of nitromethane. The hexane phase was evaporated and yielded 1.03 g of crude 1,2,3,4-tetramethoxy-5-methyl-6-((2E,6E,10E,14E,18E, 22E,26E,30E)-3,7,11,15,19,23,27,31,35-nonamethyl-hexatriaconta-2,6,10,14,18,22,26,30,34-nonaenyl)-benzene (tetramethoxy-CoQ9) as a colorless oil, which was purified by column chromatography on 30 g silica (elution with n-hexane/ethyl acetate=99:1, v/v) yielding 280 mg of a colorless oil which crystallized upon standing. Yield:32%; purity 94%.

In a similar way tetramethoxy-CoQ9 was obtained in 62.9% yield using bismuth triflate as catalyst at 50° C. for 12 hours reaction time in nitromethane/heptane (25/50, v/v).

Oxidation of the phenol to the corresponding 1,4-quinone (CoQ9) was effected as described in Synthesis 1991, 1130-1136.

EXAMPLE 7

Preparation of CoQ9

In a 100 ml flask equipped with a thermometer, a reflux condenser and a stir bar 1.17 g (6.35 mmol) of 2,3-dimethoxy-6-methyl-1,4-hydroquinone (DMMHQ) were dissolved in 6 ml of nitromethane and mixed with 0.83 g (1.27 mmol) of solanesol dissolved in 12 ml of heptane. After addition of 369 μl of aqueous 1.3 w % H$_3$O$_{40}$PW$_{12}$ solution in nitromethane to the liquid-liquid two-phase system, the mixture was heated to 40° C. (internal temperature) for 3 hours. After cooling to room temperature, the layers were separated. The heptane phase was washed with 3 ml of CH$_3$NO$_2$. The heptane-phase was stirred 1 hour at room temperature with 0.7 g of Ag$_2$O (3 mmol) and 0.05 ml of CH$_3$COOH (0.9 mmol) to oxidize the alkylation product to CoQ9. The suspension was filtered over Speedex, the orange solution was concentrated in vacuo (40° C., 100→10 mbar). The crude product (0.97 g) was analyzed by HPLC to contain: 2.1% 2,3-dimethoxy-6-methyl-1,4-quinone about 18.7% dienes/dimers; 0.9% solanesol; 0.2% ubihydroquinone; 65.6% CoQ9. The conversion of solanesol is 99% and the yield of CoQ9 63.0%.

EXAMPLE 8

Preparation of CoQ10

In a 100 ml flask equipped with a thermometer, a reflux condenser and a stir bar 2.41 g (11.75 mmol) of 2,3,4-trimethoxy-6-methylphenol (TMMP) were dissolved in 13 ml of nitromethane and mixed with 1.84 g (2.35 mmol) of isodecaprenol solved in 25 ml of heptane. After addition of 1.39 mg (0.002 mmol) bismuth trifluoromethane sulfonate to the liquid-liquid two-phase system, the mixture was heated to 46° C. (internal temperature) for 12 hours. After cooling to room temperature, the layers were separated. The orange solution was concentrated in vacuo (40° C., 100→10 mbar). The crude product (2.38 g) was analyzed by HPLC to contain: 15.9% TMMP; 40.7% 3-((2E/Z,6E,10E,14E,18E,-22E,26E,30E, 34E)-3,7,11,15,19,23,27,31,35,39-decamethyl-tetraconta-2, 6,10,14,18,22,26,30,34,38-decacaenyl)-4,5,6-trimethoxy-2-methyl-phenol ("trimethoxy-CoQ10"). The conversion of isodecaprenol was 100%, and the yield of "trimethoxy-CoQ10" 46.8% (E:Z=96.4).

The oxidation of the "trimethoxy-CoQ10" with $FeCl_3 \cdot 6H_2O$ to from COQ10 was effected as follows:

In a 100 ml flask 1.09 g of "trimethoxy-CoQ10" (0.91 mmol, 73.3%) were dissolved in 4.1 ml of dichloromethane and 4.1 ml of acetonitrile at 0° C. To this solution 2.46 g of $FeCl_3$ hexahydrate (9.0 mmol, commercial from Riedel de Haen) in 8.2 ml of acetonitrile were added at 0-5° C. After half an hour at 0-5° C., 60 ml of deionised water were added and the orange emulsion after addition of 60 ml $NaHCO_3$ solution (5%) was extracted with 250 ml of ether. The water layer was again extracted with 60 ml of ether. The combined ether phases were dried over $Na_2SO_4$ and concentrated at 35° C. (20→10 mbar). The crude product, CoQ10 (orange oil, 1.09 g, 100%), was analysed by HPLC. E/Z-ratio=95.8:4.2.

EXAMPLE 9

Preparation of "Trimethoxy-CoQ9"

In a 100 ml flask equipped with a thermometer, a reflux condenser and a stir bar 2.60 g (12.65 mmol) of 2,3,4-trimethoxy-6-methyl-phenol were dissolved in 13 ml of nitromethane and mixed with 1.65 g (2.53 mmol) of solanesol solved in 25 ml of heptane. After addition of 1.62 mg (0.0025 mmol) of bismuth trifluoromethane sulfonate to the liquid-liquid two-phase system, the mixture was heated to 50° C. (internal temperature) for 12 hours. After cooling to room temperature, the layers were separated. The heptane-phase was washed with 5 ml of $CH_3NO_2$. The solution was concentrated in vacuo (40° C., 100→10 mbar), and the crude product (2.18 g) was chromatographed over 100 g silica gel in cyclohexane/ethyl acetate (95:5,v/v).

After evaporation of the solvent in vacuo 1.39 g of a yellow oil was obtained from the main fraction which was identified to be 2,3,4-trimethoxy-6-methyl-5-((2E,6E,10E,14E,22E, 26E,30E)-3,7,11,15,19,23,27,31,35-nonamethyl-hexatria-conta-2,6,10,14,18,22,26,30,34-nonaenyl)-phenol ("trimethoxy-CoQ9").

In analogy to the method of Example 8 "trimethoxy-CoQ9" was oxidized to CoQ9.

EXAMPLE 10

Preparation of "Tetramethoxy-CoQ9"

In a 100 ml flask equipped with a thermometer, a reflux condenser and a stir bar 2.64 g (12.32 mmol) 2,3,4,5-tetramethoxytoluene were suspended in 13 ml of nitromethane and mixed with 1.61 g (2.46 mmol) of solanesol solved in 25 ml of heptane. After addition of 1.60 mg (0.0024 mmol) of bismuth trifluoromethane sulfonate to the liquid-liquid two-phase system, the mixture was heated to 50° C. (internal temperature) for 12 hours. After cooling to room temperature, the layers were separated. The heptane-phase was washed with 5 ml of $CH_3NO_2$. The solution was concentrated in vacuo (40° C., 100→10 mbar), and the crude product (2.48 g) was chromatographed over 100 g silica gel in cyclohexane/ethyl acetate 95:5, v/v.

After evaporation of the solvent in vacuo 0.92 g of "tetramethoxy-CoQ9" as a yellow oil was obtained and analyzed to be 1,2,3,4-tretramethoxy-5-methyl-6-((2E,6E,10E,14E, 18E,22E,26E,30E)-3,7,11,15,19,23,27,31,35-nonamethyl-hexatriaconta-2,6,10,14,18,22,26,30,34-nonaenyl)-benzene.

The invention claimed is:

1. A process for the preparation of ubihydroquinones and ubiquinones of the formula

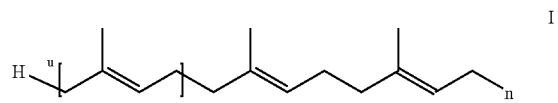

wherein U is the residue of a hydroquinone or quinone of formula

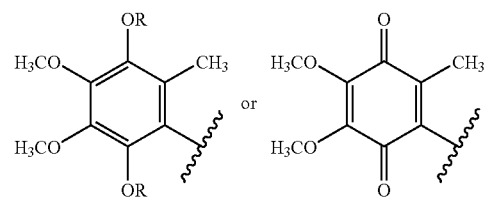

wherein R independently from each other are hydrogen or a lower alkyl group or both are tri-(lower alkyl)-silyl, lower alkanoic acyl groups or groups of the general formula —[$(CH_2)_qO$]$_r$—$(CH_2)_p$—O—$(CH_2)_m$—H,
m is 1 or 2; n is an integer of 6 to 10;
p is 1 or 2; q is 1 or 2 and r is 0 or 1,
which process is characterized by reacting an isoprenol of formula

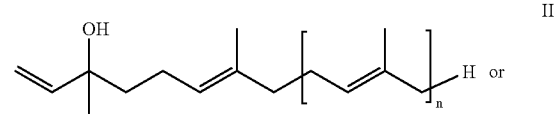

a prenol of formula

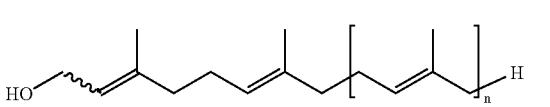

or a corresponding X-derivative, wherein OH is replaced by X and X is a leaving group,
with a hydroquinone or derivative thereof of formula

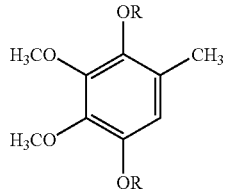

IV in an organic solvent in the presence of 0.005-1.0 mol %, relative to the isoprenol/prenol, of a catalyst which is a Broensted-acid, a Lewis-acid from the group consisting of a salt of Bi or In or an element of group 3 of the periodic table of the elements, a heteropoly acid, an NH— or a CH-acidic compound and optionally oxidizing the ubihydroquinone obtained by the condensation.

2. The process of claim 1 wherein the catalyst is present in an amount of 0.05-0.7 mol %.

3. The process of claim 1 wherein the catalyst is present in an amount of 0.1-0.5 mol %.

4. The process of claim 1 wherein n is 8.

5. The process of claim 1 wherein the compound of formula IV is 2,5-dihydroxy-3,4-dimethoxy-toluene.

6. The process of claim 1 wherein the compound of formula IV is 2-hydroxy-3,4,5-trimethoxy-toluene.

7. The process of claim 1 wherein the compound of formula IV is 2,3,4,5- tetramethoxytoluene.

8. The process of claim 1 wherein the compound of formula I is a hydroquinone.

9. The process of claim 1 wherein the compound of formula I is a quinone.

10. The process of claim 1 wherein the organic solvent is nitromethane/heptane.

11. A process for the preparation of ubihydroquinones and ubiquinones of the formula

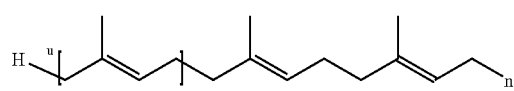

I wherein U is the residue of a hydroquinone or quinone of formula

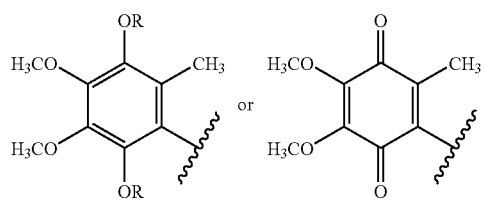

wherein R independently from each other are hydrogen or a lower alkyl group or both are tri-(lower alkyl)-silyl, lower alkanoic acyl groups or groups of the general formula $-[(CH_2)_qO]_r-(CH_2)_p-O-(CH_2)_m-H$,
m is 1 or 2; n is an integer of 6 to 10;
p is 1 or 2; q is 1 or 2 and r is 0 or 1, which process is characterized by reacting an isoprenol of formula

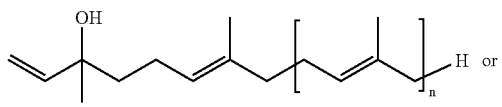

II a prenol of formula

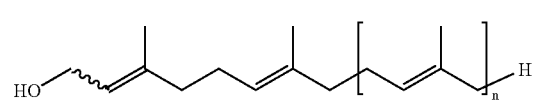

III or a corresponding X-derivative, wherein OH is replaced by X and X is a leaving group,
with a hydroquinone or derivative thereof of formula

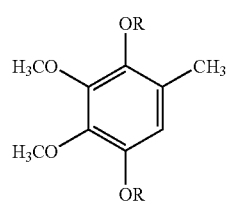

IV in an organic solvent in the presence of 0.005-1.0 mol %, relative to the isoprenol/prenol, of a catalyst which is a Broensted-acid, a Lewis-acid from the group consisting of a salt of Bi or In or an element of group 3 of the periodic table of the elements, a heteropoly acid, an NH— or a CH-acidic compound and optionally oxidizing the ubihydroquinone obtained by the condensation, wherein the catalyst is a chloride or trifluoro-methanesulfonate of Bi, In, Sc, Y, La or an element of the lanthanoides.

12. A process for the preparation of ubihydroquinones and ubiquinones of the formula

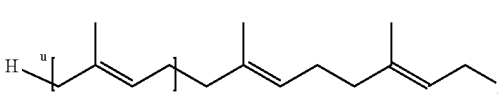

I wherein U is the residue of a hydroquinone or quinone of formula

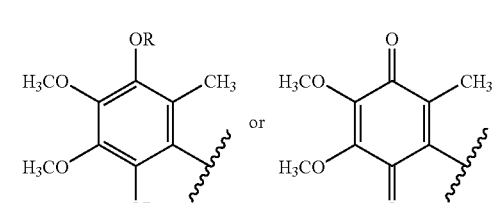

wherein R independently from each other are hydrogen or a lower alkyl group or both are tri-(lower alkyl)-silyl, lower alkanoic acyl groups or groups of the general formula —[(CH$_2$)$_q$O]$_r$—(CH$_2$)$_p$—O—(CH$_2$)$_m$—H,
m is 1 or 2; n is an integer of 6 to 10;
p is 1 or 2; q is 1 or 2 and r is 0 or 1,
which process is characterized by reacting an isoprenol of formula

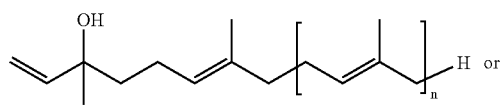

a prenol of formula

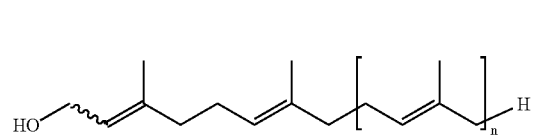

or a corresponding X-derivative, wherein OH is replaced by X and X is a leaving group,
with a hydroquinone or derivative thereof of formula

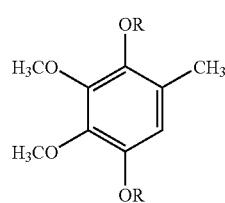

in an organic solvent in the presence of 0.005-1.0 mol %, relative to the isoprenol/prenol, of a catalyst which is a Broensted-acid, a Lewis-acid from the group consisting of a salt of Bi or In or an element of group 3 of the periodic table of the elements, a heteropoly acid, an NH— or a CH-acidic compound and optionally oxidizing the ubihydroquinone obtained by the condensation, wherein the catalyst is H$_3$PW$_{12}$O$_{40}$.

13. A process for the preparation of ubihydroquinones and ubiquinones of the formula

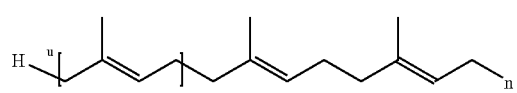

wherein U is the residue of a hydroquinone or quinone of formula

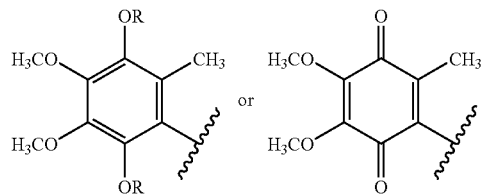

wherein R independently from each other are hydrogen or a lower alkyl group or both are tri-(lower alkyl)-silyl, lower alkanoic acyl groups or groups of the general formula —[(CH$_2$)$_q$O]$_r$—(CH$_2$)$_p$—O—(CH$_2$)$_m$—H,
m is 1 or 2; n is an integer of 6 to 10;
p is 1 or 2; q is 1 or 2 and r is 0 or 1,
which process is characterized by reacting an isoprenol of formula

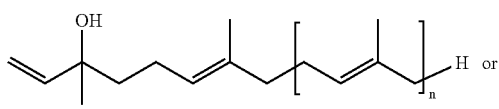

a prenol of formula

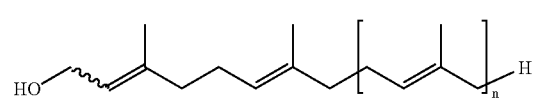

or a corresponding X-derivative, wherein OH is replaced by X and X is a leaving group,
with a hydroquinone or derivative thereof of formula

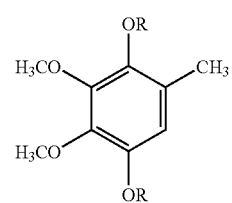

in an organic solvent in the presence of 0.005-1.0 mol %, relative to the isoprenol/prenol, of a catalyst which is a Broensted-acid, a Lewis-acid from the group consisting of a salt of Bi or In or an element of group 3 of the periodic table of the elements, a heteropoly acid, an NH— or a CH-acidic compound and optionally oxidizing the ubihydroquinone obtained by the condensation, wherein the catalyst is a perfluoro lower-alkylsulfonyl imide.

14. A process for the preparation of ubihydroquinones and ubiquinones of the formula

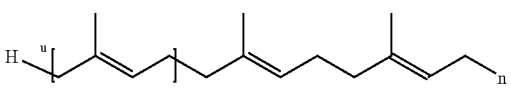

wherein U is the residue of a hydroquinone or quinone of formula

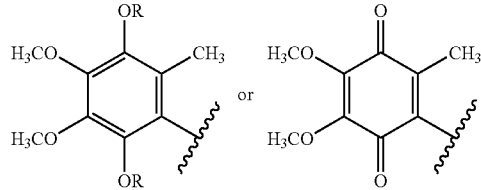

wherein R independently from each other are hydrogen or a lower alkyl group or both are tri-(lower alkyl)-silyl, lower alkanoic acyl groups or groups of the general formula —[(CH$_2$)$_q$O]$_r$—(CH$_2$)$_p$—O—(CH$_2$)$_m$—H, m is 1 or 2; n is an integer of 6 to 10;

p is 1 or 2; q is 1 or 2 and r is 0 or 1,
which process is characterized by reacting an isoprenol of formula

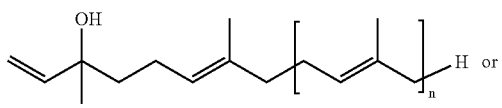

a prenol of formula

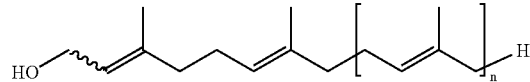

or a corresponding X-derivative, wherein OH is replaced by X and X is a leaving group,
with a hydroquinone or derivative thereof of formula

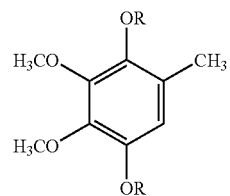

in an organic solvent in the presence of 0.005-1.0 mol %, relative to the isoprenol/prenol, of a catalyst which is a Broensted-acid, a Lewis-acid from the group consisting of a salt of Bi or In or an element of group 3 of the periodic table of the elements, a heteropoly acid, an NH— or a CH-acidic compound and optionally oxidizing the ubihydroquinone obtained by the condensation, wherein the catalyst is a perfluoro lower-alkylsulfonyl methane.

* * * * *